(12) United States Patent
Kwon et al.

(10) Patent No.: US 7,730,769 B1
(45) Date of Patent: Jun. 8, 2010

(54) CAPILLARY VISCOMETERS FOR USE WITH NEWTONIAN AND NON-NEWTONIAN FLUIDS

(76) Inventors: Kyung C. Kwon, 1157 Jenkins Dr., Auburn, AL (US) 36830; Nader Vahdat, 312 N. Gay St., Auburn, AL (US) 36830; Tamara M. Floyd-Smith, 67 Maple Creek Dr., Newnan, GA (US) 30263; Legand L. Burge, Jr., 9410 Alysbury Pl., Montgomery, AL (US) 36117; Paul Jones, 1496 Jonquilmeadow Dr., Cincinnati, OH (US) 45240

( * ) Notice: Subject to any disclaimer, the term of this patent is extended or adjusted under 35 U.S.C. 154(b) by 606 days.

(21) Appl. No.: 11/439,699

(22) Filed: May 24, 2006

(51) Int. Cl.
*G01N 11/04* (2006.01)
*G01N 11/06* (2006.01)

(52) U.S. Cl. ..................... 73/54.05; 73/54.07

(58) Field of Classification Search ............... 73/53.01, 73/54.07, 54.01, 54.05
See application file for complete search history.

(56) References Cited

U.S. PATENT DOCUMENTS

| | | | |
|---|---|---|---|
| 4,442,704 A * | 4/1984 | Swearingen | 73/54.09 |
| 4,637,250 A | 1/1987 | Irvine, Jr. | |
| 4,852,388 A | 8/1989 | Park | |
| 4,878,378 A | 11/1989 | Harada | |
| 5,327,778 A | 7/1994 | Park | |
| 5,331,843 A | 7/1994 | Gramatte | |
| 6,019,735 A | 2/2000 | Kensey | |
| 6,322,524 B1 | 11/2001 | Kensey | |
| 6,428,488 B1 * | 8/2002 | Kensey et al. | 600/573 |
| 6,470,736 B2 * | 10/2002 | Price | 73/54.04 |
| 6,484,565 B2 | 11/2002 | Shin | |
| 6,523,396 B2 | 2/2003 | Shin | |
| 6,571,608 B2 | 6/2003 | Shin | |
| 6,624,435 B2 | 9/2003 | Kensey | |
| 2001/0039828 A1 | 11/2001 | Shin | |
| 2002/0148282 A1 * | 10/2002 | Hajduk et al. | 73/54.07 |
| 2002/0184941 A1 * | 12/2002 | Shin et al. | 73/54.01 |

* cited by examiner

*Primary Examiner*—John Fitzgerald
(74) *Attorney, Agent, or Firm*—Bradley Arant Boult Cummings LLP

(57) ABSTRACT

The present disclosure describes a viscometer for measurements of both Newtonian and non-Newtonian fluids. In one embodiment, the viscometer comprises (i) a storage reservoir to store a test fluid, (ii) at least one drain tube assembly comprising a capillary drain tube, (iii) a collector for collecting said test fluid, and (iv) a detector. In addition, its novel viscosity equations suitable for the described viscometers are provided and illustrated for the application to Newtonian fluids and non-Newtonian fluids.

6 Claims, 10 Drawing Sheets

CAPILLARY VISCOMETERS FOR USE WITH NEWTONIAN AND NON-NEWTONIAN FLUIDS

BACKGROUND

A fluid can be defined as a substance that undergoes continuous deformation, when subjected to a shear stress. The resistance offered by a real fluid to such deformation is called its viscosity. All fluids have a viscosity and this property causes friction (1). The viscosity of a Newtonian fluid is constant, if static pressure and temperature are fixed. Rheological data are indispensable in the design of pumps, compressors, heat exchangers, packed columns, fluidized beds, distillation columns, pipelines, decanters, and many other pieces of equipment. In addition, rheological properties are utilized in the quality control of many consumer products. Certain materials are more acceptable to consumers if they have specific rheological properties (2).

In order to fully determine the viscosity values of a fluid, careful experimentation is required. Temperature and pressure affect viscosity of a fluid. Effects of pressure on viscosity of a fluid are negligible at pressures less than 40 atmospheres, and the viscosity of fluids is not significantly affected by relatively low pressure (3). Viscosity of Newtonian fluids is determined by measuring the shear stress at one known shear rate, whereas that of all non-Newtonian fluids is determined at more than one shear rate.

There are two main groups of viscometers that may be used to determine the viscosity of a fluid. One type of a viscometer is designed so that a fluid flows through a tube, channel or orifice, while the other type of a viscometer is constructed so that a fluid is sheared between moving surfaces (4). Several forms of viscometers have been constructed for the determination of viscosity from knowledge of the pressure drop-flow rate relationship for a tube. Such a flow may be achieved simply as a result of gravitational head. This type of viscometer is not very suitable for measurements with non-Newtonian fluids, not only because of the non-uniform shear stress across the tube section, but also because the rate of flow through the tube varies with time as the level falls. To overcome these shortcomings, a constant velocity of a fluid through a tube is maintained by pressure from a gas reservoir. For this type of a viscometer, ratios of the length to the diameter of a tube normally exceed 50 to eliminate the end effects of the tube (4). Although a few capillary tube viscometers (sometimes called extrusion rheometers) are commercially available, it is common practice to construct them in the laboratory. In constructing such viscometers, several capillary tubes with a range of lengths and diameters are needed. Tubes with internal diameters from $\frac{1}{32}$ inch to $\frac{1}{4}$ inch are typically used (5).

James et al. (6) reported a consistent set of high precision viscosity data for water at various temperatures and for 20, 30 and 40% (by weight) sucrose solutions. These were obtained using a glass capillary viscometer with an extensively flared capillary to neglect the kinetic energy correction term for this viscometer. These data are recommended as reliable standards for capillary viscometer calibration. Sirivat (7) described the results of an experimental investigation on the flow of a non-Newtonian fluid between rotating parallel disks. These results are qualitatively different from those exhibited by linearly viscous flows of the non-Newtonian fluid, where exceedingly high velocity gradients appear. Jimeneza and Kostic (8) developed, designed, and fabricated an innovative, Couette-type viscometer/rheometer with the main objective being to measure viscosity and elastic properties of low-viscous, non-Newtonian, and visco-elastic fluids, like dilute polymer solutions. Shackelton and Green (2) fabricated an on-line viscometer that has no moving mechanical parts. Measurements of the differential pressure developed along the measurement section and the temperature of the fluid are combined with the axial velocity of the test fluids to determine their mass/volume flow rates and viscosity values of both glucose syrup and melted chocolate. Chocolate exhibits non-Newtonian and glucose syrup exhibits Newtonian behavior.

However, the art is lacking an improved viscometer capable of measuring viscosity of both Newtonian and non-Newtonian fluids as described in the present disclosure. The present disclosure provides for a multiple capillary viscometer, a dual capillary viscometer, and a single capillary viscometer. In addition, the viscosity equations suitable for the described viscometers are provided and illustrated for the application to Newtonian fluids and non-Newtonian fluids. The test materials for the viscosity equation include 50% (by weight) sucrose aqueous solution as an exemplary Newtonian fluid and carboxymethylcellulose (CMC) aqueous solutions as exemplary non-Newtonian fluids.

DETAILED DESCRIPTION

Figure 1:
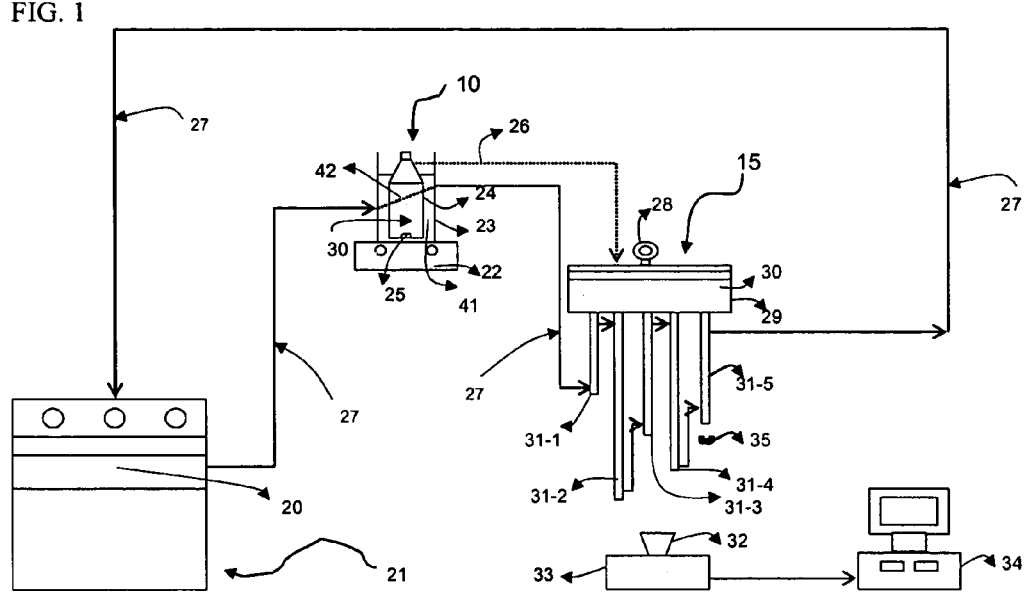
FIG. 1 is a schematic diagram of one embodiment of a multiple capillary viscometer of the present disclosure for use with Newtonian fluids and non-Newtonian fluids using five capillary drain tubes in different lengths.

A wide variety of viscometers such as capillary type, glass tube type, rotational type, falling ball type, cup-type, and oscillatory type (4, 5, 12, and 13) are available for the measurement of viscosity. However, the art is lacking a simple-to-use and operator-friendly viscometer for the measurement of Newtonian fluids and non-Newtonian fluids as disclosed herein. Several embodiments of the novel viscometer as disclosed herein are illustrated in FIGS. 1 through 8. In addition, the viscosity equations for use with the viscometers disclosed are also provided.

In a general description, a viscometer assembly disclosed comprises: (i) a storage reservoir to store a test fluid being analyzed, (ii) at least one drain tube assembly, each drain tube assembly comprising one inner capillary drain tube surrounded by a protecting metal casing surrounded by an insulated jacket, (iii) a collector for collecting said test fluid, and (iv) a detector. In one embodiment, the inner capillary drain tube in the absence of the protecting metal casing is surrounded directly by an insulated jacket. The viscometer may also comprise other accessory components to aid in operation such as (v) a second reservoir comprising a first storage tank for holding additional quantities of the test fluid being analyzed and a second storage tank for holding the first storage tank, a heating/cooling element, and another temperature regulating fluid in a space between the first storage tank and a second storage tank and (vi) a circulator, which may comprise a temperature regulator and a temperature regulating fluid, for circulating and/or storing the temperature regulating fluid. In one embodiment, a vertical capillary viscometer is provided comprising multiple drain tube assemblies, with each of the drain tube assemblies having an inner capillary drain tube and the viscometer is referred to as a multiple vertical capillary (MVC) viscometer. In an alternate embodiment, a vertical capillary viscometer is provided comprising two drain tubes assemblies, with each of the drain tube assemblies having an inner capillary drain tube and the viscometer is referred to as a dual vertical capillary (DVC) viscometer. In yet another embodiment, a vertical capillary viscometer is provided comprising a single drain tube assembly, said drain tube assembly having an inner capillary drain tube and the viscometer is referred to as a single vertical capillary (SVC) viscometer. In embodiments where more than one capillary drain tube is present, the capillary drain tubes may have different lengths and/or different radii. Furthermore, in embodiments where more than one drain tube assembly is present, each drain tube assembly may be presented as an individual unit or as a single unit comprising each of the drain tube assemblies.

In one embodiment, the storage reservoir and/or the second storage tank of the second reservoir are made from a low-thermally conductive material. A suitable material is Plexiglas, although other materials may be used. The inner capillary drain tubes (discussed below) of each drain tube assembly are made from a material inert and non-reactive to the fluids. A suitable material is stainless steel, although other materials may be used. The inner capillary drain tube(s) of the drain tube assembly are connected to the storage reservoir such that the top ends (first end) of the inner capillary drain tube(s) are in fluid communication with the test fluid contained in the storage reservoir. The bottom ends (second end) of the inner capillary drain tube(s) are initially closed during introduction of the test fluid to the storage reservoir. After the storage reservoir is filled with the test fluid to the desired level, the test fluid is allowed to flow through the inner capillary drain tube(s) to evacuate air therein. When the air is evacuated from the capillary drain tube(s), the second ends (bottom ends) are closed to stop the flow of the test fluid. The inner capillary drain tubes of the drain tube assemblies may be closed with a tube end cap or with any type of valve device as is known in the art (such a ball-type valve).

A detector is placed beneath the second end of the inner capillary drain tube(s) of each drain tube assembly of the viscometer to detect a test fluid flowing through the capillary drain tube(s). A collector is placed on the detector to collect the test fluid. In one embodiment, the detector is a mass detector and determines the mass of the fluid flowing through the inner capillary drain tube. In such an embodiment, the detector may be calibrated to account for the weight of the collector. The detector may determine the accumulated amounts of the test fluid passing through each of the inner capillary drain tubes individually as a function of time (which time may be referred to as the drain duration time). The detector may be in communication with a processor (such as a computer) and may transmit data regarding the accumulation of the test fluid over time to the processor. The processor may further comprise a data acquisition software to aid in obtaining, storing and analyzing a data set received from the detector. In one embodiment, the data acquisition software can code the data received from the detector as a function of time to produce an experimental data set (there may be one or multiple experimental data sets for a given test condition depending on the type of viscometer used). In addition, the processor may comprise the equations for determining one rheological property or a set of rheological parameters of the test fluid, with the aid of the experimental data set. The rheological properties or the rheological parameters may vary depending on the nature of the test fluid. Such rheological properties of the Newtonian test fluid include dynamic viscosity, and the rheological parameters of the non-Newtonian test fluid include flow behavior index and consistency index. The processor may also receive input from an operator regarding the details of the test fluid being analyzed, experimental conditions (such as, but not limited to, density, temperature, and pressure of the test fluid) and conditions relating to the viscometer (such as, but not limited to, the length of the capillary drain tubes and the radius/diameter of the inner capillary drain tubes).

In one embodiment, the data acquisition begins when the inner capillary drain tube of a drain tube assembly is opened (the inner capillary drain tube is prepared as described above) and a test fluid flows from the inner capillary drain tube into the collector. The data acquisition can be activated by the operator manually or can be programmed to start when the detector measures a flow of the test fluid into the collector or when a sensor determines that the test fluid is exiting the inner capillary drain tube. Accumulated amounts of the test fluid drained from the viscometers are measured at the desired interval/time of drain duration with the detector. One or more series of data sets representing the amount of the test fluid detected by the detector at various drain durations/times are obtained with each of the inner capillary drain tubes of the viscometer. The temperature of the test fluid and the temperature of the inner capillary drain tubes may be maintained at a constant temperature. The temperature may be selected by the operator as desired. The pressure of the test fluid may also be regulated and maintained at a constant pressure. The viscometer may also be operated at atmospheric pressure, where the gauge pressure $P_g$ is zero. The pressure may be selected by the operator as desired.

The viscometers disclosed may be used with both Newtonian fluids and non-Newtonian fluids. Applying the equations disclosed to the one or more experimental data sets, one rheological property and a set of rheological parameters of the test fluid can be determined. For example, when using a MVC viscometer with five inner capillary drain tubes of five drain tube assemblies, quintuple dynamic viscosity values may obtained for Newtonian fluids for a given set of conditions, or a single characterization of the flow behavior of non-Newtonian fluids may be obtained for a given set of conditions. The MVC viscometer can be converted easily into a SVC viscometer by using only one capillary drain tube of the MVC viscometer. The inner capillary drain tube to be used may be selected depending on the viscosity of the test fluid being tested. Short capillary drain tubes are suitable for relatively high viscous Newtonian and non-Newtonian fluids, whereas long capillary drain tubes are suitable for relatively low viscous Newtonian and non-Newtonian fluids, since the viscosity equations are developed for laminar flows. The MVC viscometer can also be converted easily into a DVC viscometer by using only a pair of capillary drain tubes of the MVC viscometer to measure duplicate viscosity values for Newtonian fluids and obtain minimum data for the characterization of the flow behavior of non-Newtonian fluids.

Figure 6:
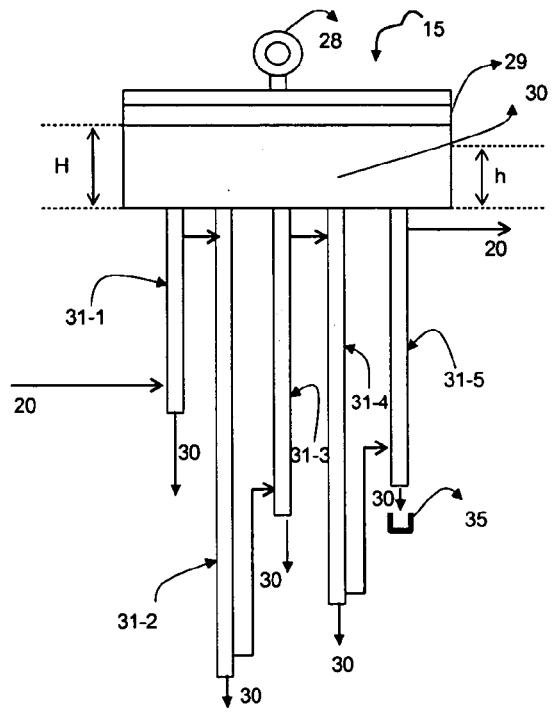
FIG. 6 is an enlarged view of one embodiment of the multiple capillary viscometer having five capillary drain tubes in different lengths.

As discussed above, several embodiments of a viscometer are disclosed in the instant specification. In one embodiment, a MVC viscometer is disclosed comprising a set of drain tube assemblies, each drain tube assembly having an inner capillary drain tube. In a specific example, a MVC viscometer is disclosed with 5 drain tube assemblies, with each drain tube assembly having an inner capillary drain tube and is illustrated in FIGS. 1 and 6. The inner capillary drain tubes may have different lengths and/or may have different radii. Alternatively, the capillary drain tubes may have different lengths and have the same radii. In the example described below, the radii of the capillary drain tubes are constant at 0.05114 cm, and the lengths of the capillary drain tubes are 27.5, 33.4, 37.6, 46.9, and 56.4 cm. The ratio of the length to the diameter of the capillary drain tube of the MVC viscometer is 268-551 to one to negate the end effects on completion of final velocity distribution of a laminar flow in the entrance region of the capillary drain tubes. The equivalent radius and the height of the storage reservoir are 5.55 cm and 9.08 cm, respectively. Alternative values for those recited above may be used as would be known to one of ordinary skill in the art.

In the embodiment illustrated in FIGS. 1 and 6, the five drain tube assemblies of the MVC viscometer 15, each drain tube assembly containing the inner capillary drain tube, are designated 31-1, 31-2, 31-3, 31-4 and 31-5 and are used for the determination of a rheological property or a set of rheological parameters of a test fluid 30 contained in a reservoir 29. The test fluid 30 may be a Newtonian fluid or a non-Newtonian fluid. The inner capillary drain tube is in fluid communication with the storage reservoir 29. A MVC viscometer assembly containing the MVC viscometer 15 may further comprises a detector 33, a collector 32, a processor 34 in communication with the detector 33, a second reservoir 10, and a circulator 21 in fluid communication with the second reservoir 10. The second reservoir 10 comprises a first storage tank 24 for storing an additional supply of the test fluid 30, a second storage tank 23 for storing another temperature regulating fluid 41, and a heating/cooling element 42 submerged into the other temperature regulating fluid 41 in a space between the first storage tank 24 and the second storage tank 23.

The bottom of the storage reservoir 29 is fluidly connected to an inlet 31-1A (also referred to as the first end) of the inner capillary drain tube of the drain tube assembly 31-1 (FIGS. 5 and 6). The remaining inner capillary drain tubes have inlets 31-2A, 31-3A, 31-4A, and 31-5A, and are connected as described for the assembly 31-1. The capillary drain tubes in this embodiment have the same radius $R_o$ and a different length L, and are positioned vertically with respect to the reservoir 29. An outlet 31-1B (also referred to as the second end) of the inner capillary drain tube of the drain tube assembly 31-1 is open to the atmosphere and positioned over a collector 32 during use. The remaining inner capillary drain tubes of the drain tube assemblies 31-2, 31-3, 31-4, and 31-5 also have an outlet 31-2B, 31-3B, 31-4B, and 31-5B open to the atmosphere and are positioned over the collector 32 during use. In one embodiment, a common collector 32 and a common detector 33 are used for each capillary drain tube and measurements are obtained serially.

Figure 4:
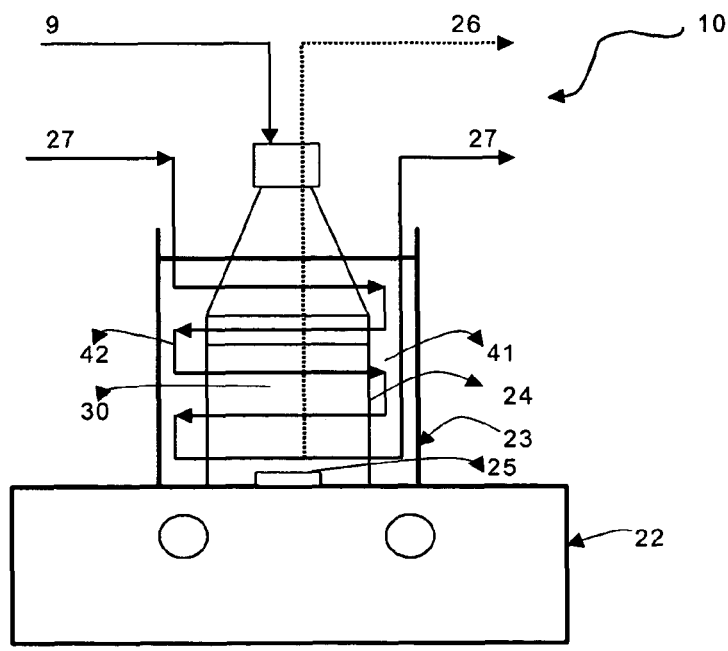
FIG. 4 is an enlarged view of one embodiment of a second reservoir for use with the various viscometers disclosed herein.
Figure 5A:
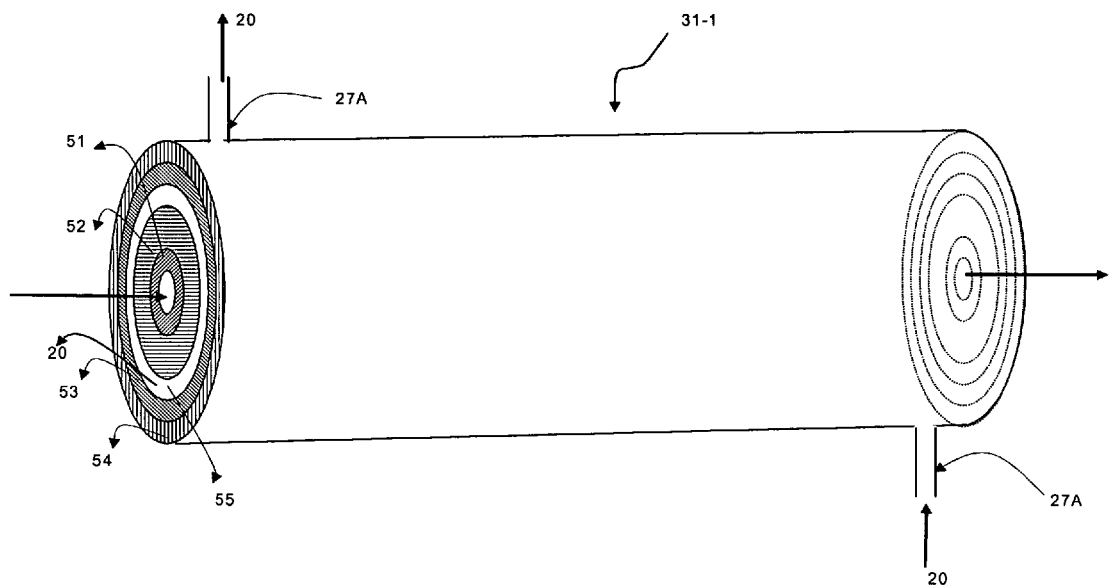
FIG. 5A is a cross-sectional view of one embodiment of a drain tube assembly comprising a capillary drain tube surrounded by an annular layer of metal casing and an insulated jacket for use with the various viscometers disclosed herein.
Figure 5B:
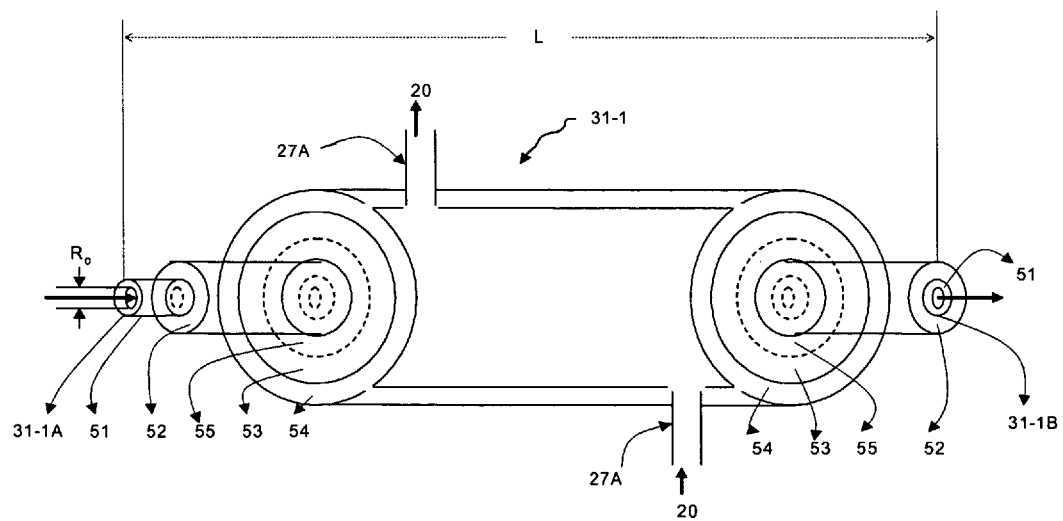
FIG. 5B is a side view of one embodiment of a drain tube assembly comprising a capillary drain tube surrounded by an annular layer of metal casing and an insulated jacket for use with the various viscometers disclosed herein.

One embodiment of the structure of a drain tube assembly will now be described in greater detail. FIGS. 5A and 5B illustrate one embodiment of the design of the drain tube assembly. Although only one drain tube assembly is illustrated, the remaining drain tube assemblies are understood to have the identical structure, with only the lengths and radii possibly being different. The drain tube assembly 31-1 is shown comprising an inner capillary drain tube 51 surrounded by a protecting metal casing 52 (a form of the metal casing 52 may be cylindrical) a jacket 53 and an insulating material 54. The metal casing 52 is surrounded by the jacket 53, which further is wrapped with the insulating material 54. A space 55 between the metal casing 52 and the jacket 53 is created to receive the temperature regulating fluid 20 as discussed below. The temperature-regulating fluid 20 is circulated in the space 55 between the outside surface of the metal casing 52 and the inside surface of the jacket 53 and is circulated through the viscometer as shown by the line 27 and ports 27A. The use of the metal casing 52 and the insulating material 54 are optional, however; when not used the space 55 may be created between the inner capillary drain tube 51 and the jacket 53. The temperature of the test fluid 30 may be maintained at a desired temperature and/or adjusted to a desired temperature using a temperature regulating system as described below. The circulator 21 may also contains the temperature regulating fluid 20 to maintain the test fluid 30 at a desired temperature. The circulator 21 is capable of heating/cooling the temperature regulating fluid 20 to a desired temperature. The circulator 21 supplies the temperature regulating fluid 20 to a heating/cooling element 42 of a second reservoir 10 (see FIG. 4) via line 27. The heating/cooling element 42 is submerged into the other temperature regulating fluid 41 in a space between the first storage tank 24 and the second storage tank 23 to maintain the temperatures of both the test fluid 30 in the first storage tank 24 and the other temperature regulating fluid 41 in the second storage tank 23. The first storage tank 24 may have an element to stir the test fluid 30 to aid in a uniform temperature distribution and to create a homogenous mixture. In FIG. 4, a magnetic stirring bar 25 and a magnetic stirrer 22 are illustrated to serve such purposes, although other arrangements may be used. The temperature regulating fluid 20 is also used to maintain the temperature of the capillary drain tubes at a desired temperature via line 27 as shown in FIGS. 1 and 4 (see discussion below for additional details). The first storage tank 24 is in fluid communication with the storage reservoir 29 via line 26. In one embodiment, the test fluid 30 is transferred from the first storage tank 24 to the storage reservoir 29 by applying helium pressure to the first storage tank 24 via line 9 (see FIG. 4). The applied helium pressure causes the test fluid 30 to flow through line 26. The second reservoir 10 and the components thereof are illustrated in FIG. 4 in greater detail.

The temperature-regulating fluid 20 is also circulated from the heating/cooling element 42 of the second reservoir 10 to the space 55. In this manner, the temperature of the test fluid 30 flowing through each inner capillary drain tube may also be regulated. Furthermore, the pressure at the level of the test fluid 30 in the reservoir 29 can be controlled with the helium pressure and monitored with a pressure gauge or other indicator, illustrated as a pressure gauge 28 in FIGS. 1 through 3 and 6 through 8.

It should be noted that the temperature of the test fluid 30 could be regulated and maintained at the desired temperature by other means as well, with the embodiment described above being exemplary in nature. For example, each inner capillary drain tube, the first storage tank 24, and the storage reservoir 29 could be provided with electrical heating/cooling elements or jackets to maintain and/or adjust the temperature of the test fluid 30.

Figure 7:
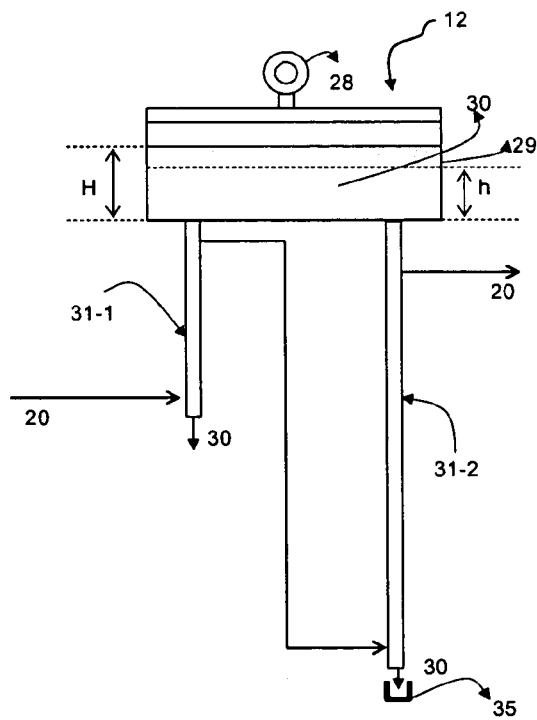
FIG. 7 is an enlarged view of one embodiment of the dual capillary viscometer having two capillary drain tubes in different lengths.
Figure 8:
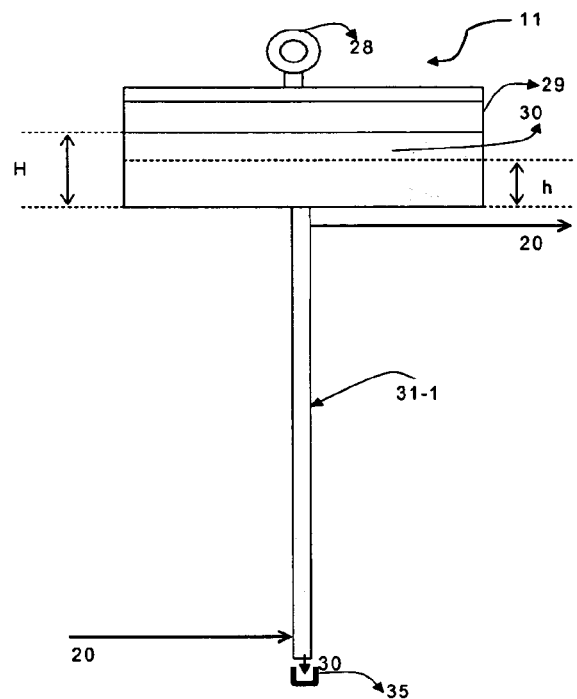
FIG. 8 is an enlarged view of one embodiment of the single capillary viscometer having single capillary drain tube.

In preparation for obtaining a rheological property or a set of rheological parameters of the test fluid 30, the test fluid 30 is introduced into the storage reservoir 29 as described. A syringe may be used to introduce the test fluid 30 in the inner capillary drain tubes of the drain tube assemblies 31-1 through 31-5 prior to operation. As described above, the test fluid 30 is allowed to flow through the inner capillary drain tubes to evacuate any air that may be trapped therein. When each inner capillary drain tube is filled with the test fluid 30, each inner capillary drain tube is closed. When the detector 33 is activated, one of inner capillary drain tubes is opened and the test fluid 30 passes through said inner capillary drain tubes via tube 51 and is collected by the collector 32. This process may be repeated individually for the remaining inner capillary drain tubes of the drain tube assemblies. At the end of the run for a given capillary drain tube, the run is terminated by de-activating the detector 33, signaling the processor 34 that the run is finished and the data set is complete for the given inner capillary drain tube. The level of the test fluid 30 in the storage reservoir 29 may be adjusted to the level measured before the run by transferring the test fluid 30 from the first storage tank 24 to the storage reservoir 29 so that the test fluid in the storage reservoir 29 is at a desired height H as shown in FIGS. 6 through 8. In one embodiment, the height H is the same before each collection run. The same experimental procedures as described above are applied to the remaining inner capillary drain tubes of the drain tube assemblies, which generate four additional series of experimental data.

During operation of the MVC viscometer 15, the collector 32 rests on a detector 33 so as to measure the amount of a test fluid 30 exiting each capillary drain tube. In one embodiment, the detector 33 is a mass detector and measures the mass of the test fluid 30. As an example, the mass detector may be a precision balance or a load cell (such as VI-3 mg electronic balance by ACCULAB Corporation of Huntingdon Valley, Pa.). The detector 33 is in communication with a processor 34. As described above, the processor may comprise data acquisition software and the equations described below, and may receive operator input relating to the test fluid 30 and/or the test conditions. As the collector 32 collects the test fluid 30 during use, the changing mass value over a drain duration time is transmitted to the processor 34 from the detector 33 for the determination of one rheological property of a Newtonian test fluid 30 or to characterize the flow behavior of a non-Newtonian fluid. In one embodiment, the mass detector 33 generates an electrical signal that corresponds to the mass variation with time. The connection between the mass detector 33 and the processor 34 may be bi-directional. Bi-directional communication allows an operator to start and stop a data acquisition from either the detector 33 or the processor 34.

Quintuple viscosity values of the Newtonian test fluid 30 can be determined with the five series of experimental data obtained at various drain duration times as described above, using the MVC viscometer. The processor 34 can then manipulate the data to generate a desired output, such as the viscosity of the test fluid 30. Five different shear rates of a non-Newtonian test fluid can be obtained from the MVC viscometer described above under a given operation condition to characterize flow behaviors of non-Newtonian fluids.

Figure 2:
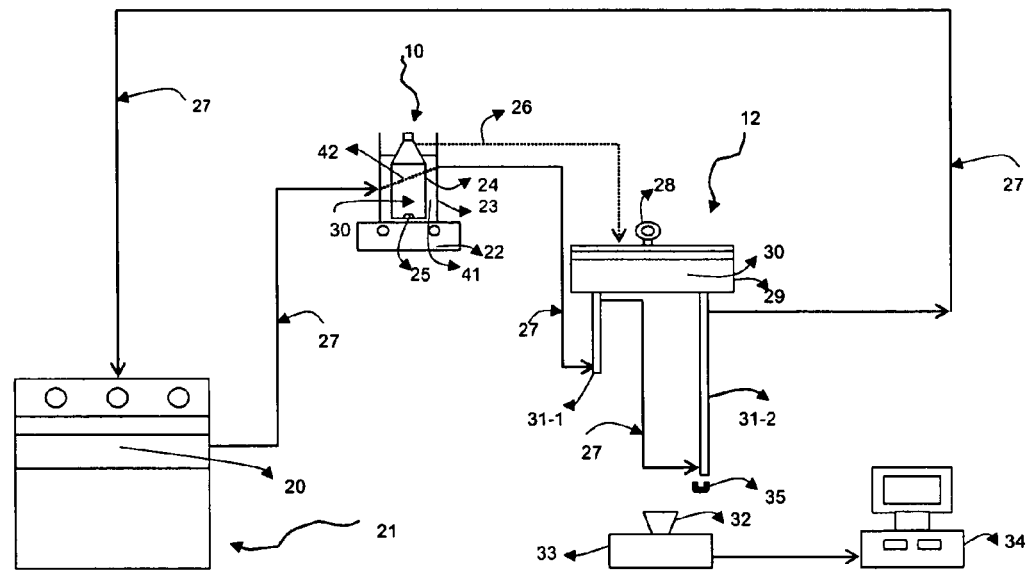
FIG. 2 is a schematic diagram of one embodiment of a dual capillary viscometer of the present disclosure for use with Newtonian fluids and non-Newtonian fluids using two capillary drain tubes in different lengths.
Figure 3:
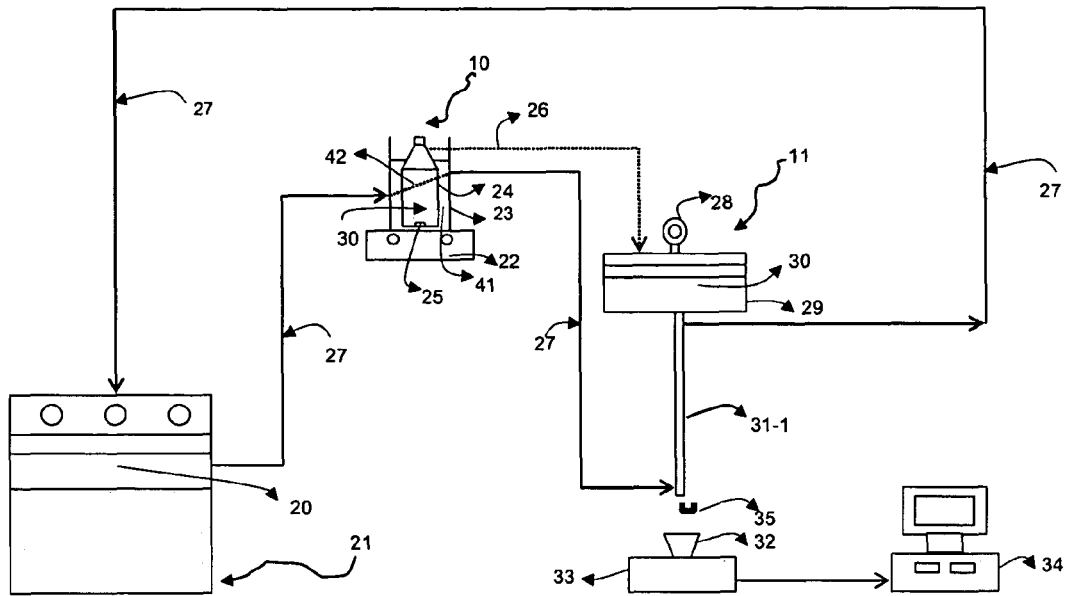
FIG. 3 is a schematic diagram of one embodiment of a single capillary viscometer of the present disclosure for use with Newtonian fluids using single capillary drain tube.

A second embodiment, the DVC viscometer having a pair of drain tube assemblies (designated 31-1 and 31-2) each having an inner capillary drain tube for determining the viscosity of either a Newtonian or non-Newtonian test fluid 30 is also described. The DVC viscometer is designated 12 and is illustrated in FIG. 2. The DVC viscometer assembly comprises the components described above for the MVC viscometer with the exception that only two inner capillary drain tubes are utilized. As discussed above, the lengths of the tubes may be different. The data collection and the analysis methods described above for the MVC viscometer are also applicable to the DVC viscometer. Using the DVC viscometer, two different shear rates and/or shear stresses of the non-Newtonian test fluid 30 can be obtained under a given operating condition to characterize flow behaviors of non-Newtonian fluids, whereas duplicate viscosity values of a Newtonian test fluid can be obtained under a given operating condition.

A third embodiment, the SVC viscometer having a single drain tube assembly (designated 31-1) having an inner capillary drain tube for determining viscosity values of a Newtonian test fluid 30 is also described. The SVC viscometer is designated 11 and shown in FIG. 3. The SVC viscometer assembly comprises the components described above for the MVC viscometer with the exception that only one inner capillary drain tube is used. The data collection and the analysis methods described above for the MVC viscometer are also applicable to the SVC viscometer. Numerous viscosity values of Newtonian fluids can be obtained from single given test condition.

A MVC viscometer 15 can be converted easily into a SVC viscometer 11 by using only one inner capillary drain tube out of five inner capillary drain tubes of the drain tube assemblies. The inner capillary drain tube used may be selected depending on viscosity of non-Newtonian and Newtonian fluids. Short capillary drain tubes are suitable for high viscous fluids, whereas long capillary drain tubes are suitable for low viscous fluids, since the viscosity equations are developed for laminar flows. The MVC viscometer 15 can be converted easily into a DVC viscometer 12 by using only a pair of inner capillary drain tubes out of five inner capillary drain tubes of the drain tube assemblies. The inner capillary drain tubes used may be selected depending on viscosity of fluids as discussed above.

Theory of Operation

Newtonian Fluids

The Newtonian model describes a fluid in which the shear stress in the radial direction $\tau_{rz}$ is directly proportional to the shear rate $dv_z/dr$. For the case of a fluid flowing in a tube of radius r, the shear stress can be expressed in terms of a velocity gradient $dv_z/dr$. The proportionality $\mu$ in Equation (1) is called the viscosity of the fluid.

$$\tau_{rz} = -\mu \frac{dv_z}{dr} \quad (1)$$

Where the following terms have the meaning as set forth below

| | |
|---|---|
| $\tau_{rz}$: | shear stress at the distance r from the center of an inner capillary drain tube |
| $\mu$: | dynamic viscosity of Newtonian fluids |
| $v_z$: | local velocity in a cylindrical tube at the distance r from the center of a drain tube |
| r: | distance from the center of a cylindrical inner capillary drain tube |

The laminar flow of fluids in circular drain tubes is analyzed by means of the momentum balance (9) to obtain Equation (2). The detailed derivation of Equation (2) is shown in the reference numbers (10) and (11). The cylindrical coordinates are used to describe positions in the inner capillary drain tubes of a MVC viscometer, a DVC viscometer, and a SVC viscometer.

$$\tau_{rz} = \rho g \left( \frac{h}{L} + \frac{P_g}{\rho g L} + 1 \right) \frac{r}{2} \quad (2)$$

where the following terms have the meaning as set forth below

| | |
|---|---|
| $\rho$: | density of a test fluid 30 |
| g: | acceleration of gravity |
| h: | level of a test fluid 30 in a reservoir 29 at a drain duration t |
| L: | length of an inner capillary drain tube 51 |
| $P_g$: | gauge pressure at the level of a test fluid 30 in the reservoir 29 |

Equation (3) is obtained by making the unsteady-state mass balance of a fluid around the reservoir of the viscometer.

$$\pi R_o^2 \rho v_{zm} = -\frac{d(\pi R^2 h \rho)}{dt} \quad (3)$$

where the following terms have the meaning as set forth below

| | |
|---|---|
| $R_o$: | inside radius of a capillary drain tube 51 |
| $v_{zm}$: | average velocity of a test fluid 30 in an inner capillary drain tube 51 |
| R: | equivalent radius of a rectangular reservoir 29 |
| t: | drain duration |
| $\pi$: | 3.1416 |

A change in the level of a test fluid 30 in the reservoir 29 at a given drain duration is very small. Often it is very difficult to read the change in the level of the test fluid 30 in the reservoir. Hence, the level of the test fluid 30 in the reservoir 29 at a given duration time is described in terms of accumulated amounts of the test fluid 30 drained from the reservoir 29 (see Equation (4)). Making a mass balance of the test fluid 30 around the reservoir 29 of the capillary viscometer derives Equation (4). Although both the "h" value (the level of the test fluid 30 in the reservoir 29) and the "m" value (accumulated amounts of the test fluid drained from the reservoir 29) are a function of "t" (drain duration), the relationship between h and m in Equation (4) is independent of drain durations.

$$h = H - \frac{m}{\pi R^2 \rho} \quad (4)$$

where the following terms have the meaning as set forth below

| H: | initial level of a test fluid in a reservoir tank |
|---|---|
| m: | accumulated amount of a test fluid drained at t |

Equation (5) is obtained with Equations (1) through (4). The detailed derivation of Equation (5) is shown in the references (10) and (11). The left-hand side of Equation (5) contains accumulated amounts of a test fluid 30 drained from the viscometer at drain durations t, while the right-hand side of the Equation (5) contains drain durations. Therefore, Equation (5) allows the calculation of the viscosity of the Newtonian test fluid 30 if the total mass of the test fluid 30 out of the reservoir at known drain duration is given.

$$-\ln\left(1 - \frac{m}{\left(H + \frac{P_g}{\rho g} + L\right)\pi R^2 \rho}\right) = \left(\frac{gR_o^4 \rho}{8\mu R^2 L}\right)(t) \quad (5)$$

Equation (5) generates numerous viscosity values of Newtonian test fluids 30 depending on number of experimental data series of accumulated amounts of Newtonian test fluids 30 drained from a capillary drain tube at various drain durations. Several series of experimental data of accumulated amounts of a Newtonian test fluid 30 drained from the reservoir 29 at various drain durations are applied to the viscosity equation of Newtonian fluids, as shown in Equation (5). Left-hand side (LHS) values of Equation (5) are plotted against drain durations. A slope of the best-fit straight line passing through the origin of the rectangular coordinates is obtained through the linear least squares method. A dynamic viscosity value is calculated with Equation (6) by substituting a density value of the Newtonian test fluid 30, the radii of both the reservoir 29 and the capillary drain tube 51, and the length of the capillary drain tube 51 into the slope value.

$$\mu = \frac{g\rho R_o^4}{8 R^2 L S} \quad (6)$$

where the following term has the meaning as set forth below

S: slope value of Equation (5)

An average velocity of a Newtonian test fluid 30 in a capillary drain tube 51 can be calculated with Equation (7) and is useful in obtaining Reynolds number for the flow of the test fluid 30 in the inner capillary drain tube 51. Equation (7) is derived with Equations (3), (4), and (5). The detailed derivation of Equation (7) is shown in the references (10) and (11).

$$v_{zm} = -\left(\frac{R}{R_o}\right)^2 \left[\ln\left(1 - \frac{m}{\pi R^2 \rho (H + L)}\right)\right] \times \left[H + L - \frac{m}{\pi R^2 \rho}\right] \frac{1}{t} \quad (7)$$

Non-Newtonian Fluids

Paints, consumer products, hygiene products, and some food products are considered as non-Newtonian fluids, which mostly follow the power law model. The power law model describes a fluid in which the shear stress in the radial direction, $\tau_{rz}$, is directly proportional to $(dv_z/dr)^n$, as shown in Equation (8). For the case of a fluid flowing in an inner capillary drain tube of radius $R_o$, the shear stress can be expressed in terms of a velocity gradient $dv_z/dr$. Substituting Equation (8) into Equation (2) produces Equations (9).

$$\tau_{rz} = k\left(-\frac{dv_z}{dr}\right)^n \quad (8)$$

where the following term has the meaning as set forth below

| k: | consistency index of power law fluids |
|---|---|
| n: | flow behavior index of power law fluids |

$$\left(-\frac{dv_z}{dr}\right) = \left(\rho g\left(\frac{h}{L} + \frac{P_g}{\rho g L} + 1\right)\frac{r}{2k}\right)^{\left(\frac{1}{n}\right)} \quad (9)$$

Equation (10) is obtained by separating the variables r and $v_z$ of Equation (9), integrating the resulting equation, and by applying the boundary condition $v_z=0$ at $r=R_o$.

$$v_z = \left(\rho g\left(\frac{h}{L} + \frac{P_g}{\rho g L} + 1\right)\frac{1}{2k}\right)^{\left(\frac{1}{n}\right)} \frac{n}{(1+n)}\left(R_o^{\left(1+\frac{1}{n}\right)} - r^{\left(1+\frac{1}{n}\right)}\right) \quad (10)$$

$$v_{zm} = \left(\rho g\left(\frac{h}{L} + \frac{P_g}{\rho g L} + 1\right)\frac{1}{2k}\right)^{\left(\frac{1}{n}\right)} \frac{n}{(1+3n)}\left(R_o^{\left(1+\frac{1}{n}\right)}\right) \quad (11)$$

The average velocity $v_{zm}$ is calculated by dividing the volumetric flow rate with the cross-sectional area, as shown in Equation (11). Substitution of Equations (4) and (11) into Equation (3) and integration of the resulting equation produce equation (12), a so-called non-Newtonian viscosity equation (NNVE).

$$\ln\left(\frac{m}{\pi R_o^3 \rho t}\right) \cong \frac{1}{n}\ln\left(\frac{\rho g R_o\left(H + \frac{P_g}{\rho g} + L\right)}{2L}\right) + \ln\left(\frac{n}{(1+3n)}\left(\frac{1}{k}\right)^{\frac{1}{n}}\right) \quad (12)$$

The left-hand side of Equation (12) contains accumulated amounts of a test fluid 30 drained from the viscometer at various drain durations, while the right-hand side of the Equation (12) contains the length of the inner capillary drain tube 51. Therefore, Equation (12) allows us to calculate the consistency index k and the flow behavior index n of a power law fluid, if amounts of the test fluid 30 out of the reservoir 29 at known drain durations are given at various lengths of the inner capillary drain tube 51 of the viscometer.

Experimental data of accumulated amounts of non-Newtonian test fluids 30 drained from various inner capillary drain tubes at various drain durations are applied to Equation (12). Left-hand side (LHS) values against the right hand-side (RHS) term containing a variable length of the inner capillary drain tube in Equation (12) are plotted. A slope and an intercept of a best-fit straight line are obtained through the linear least squares method. A flow index n value and a consistency k value of non-Newtonian test fluids 30 are calculated with Equations (13) and (14), respectively.

$$n = \frac{1}{S} \quad (13)$$

$$k = \left(\frac{n}{\exp(I)(1+3n)}\right)^n \quad (14)$$

Where the following terms have the meaning as set forth below

S: slope value of a linear least squares straight line with Equation (12)

I: intercept value of a linear least squares straight line with Equation (12)

Equation (15) describes shear rates of non-Newtonian fluids at the inside wall of an inner capillary drain tube 51. Equation (15) is obtained by substituting Equation (4) into Equation (9). Shear rates of non-Newtonian test fluids 30 at the inside wall of a capillary tube are calculated with accumulated amounts of a test fluid 30 drained from the capillary drain tube 51 of a viscometer at various drain durations, using Equation (15).

$$-\left(\frac{dv_z}{dr}\right)\bigg|_{r=R_o} = \left[\frac{\rho g R_o}{2kL}\left(H + L + \frac{P_g}{\rho g} - \frac{m}{\pi R^2 \rho}\right)\right]^{\frac{1}{n}} \quad (15)$$

Equation (16) describes shear stresses of non-Newtonian fluids at the inside wall of an inner capillary drain tube. Equation (16) is obtained by substituting Equation (15) into Equation (8). Shear stresses of non-Newtonian fluids at the inside surface of the inner capillary drain tube of a viscometer are calculated with accumulated amounts of a test fluid drained from the viscometer at various drain durations, using Equation (16).

$$(\tau_{rz})\bigg|_{r=R_o} = \frac{\rho g R_o}{2L}\left(H + L + \frac{P_g}{\rho g} - \frac{m}{\pi R^2 \rho}\right) \quad (16)$$

Equation (17) describes apparent viscosity values of non-Newtonian fluids in an inner capillary tube. Equation (17) is obtained by dividing Equation (16) with Equation (15).

$$\mu_{app} = k\left[-\left(\frac{dv_z}{dr}\right)\bigg|_{r=R_o}\right]^{(n-1)} = k\left[\frac{\rho g R_o}{2kL}\left(H + L + \frac{P_g}{\rho g} - \frac{m}{\pi R^2 \rho}\right)\right]^{\frac{(n-1)}{n}} \quad (17)$$

Examples

Figure 9:
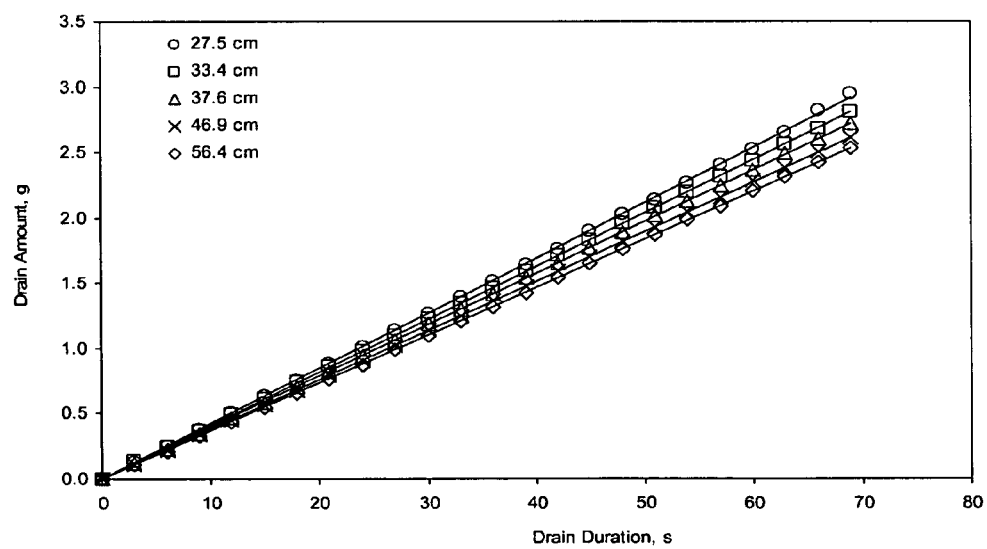
FIG. 9 shows sextuple drain amounts (in grams) of 50% (weight to weight) sucrose aqueous solution against drain durations (in seconds) at 25.91° C. using one embodiment of the multiple capillary viscometer having five capillary drain tubes in different lengths.
Figure 10:
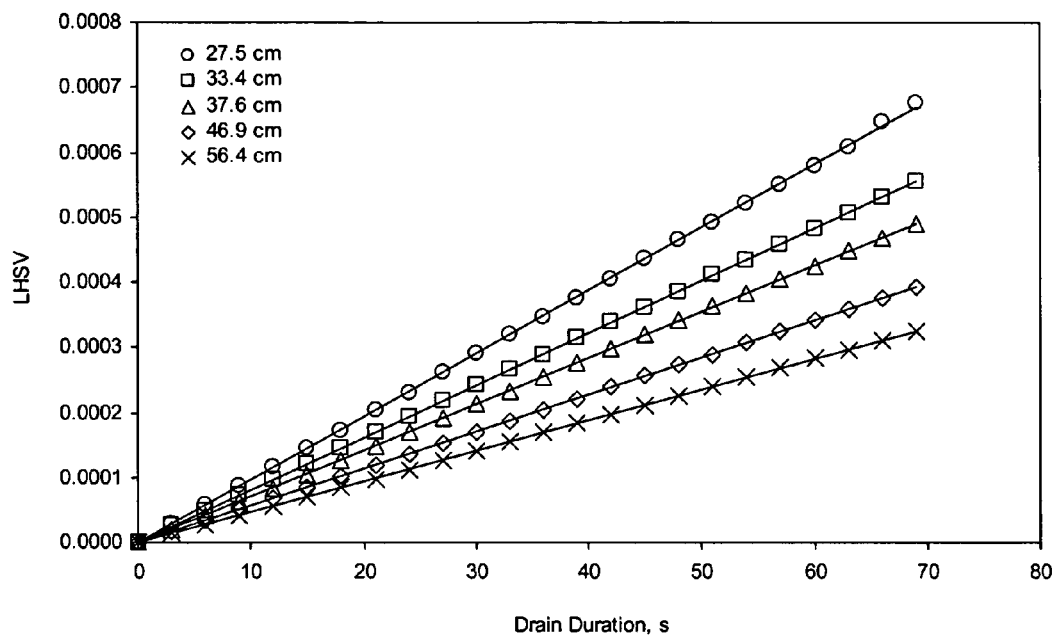
FIG. 10 shows left-hand side values (LHSV) of Newtonian viscosity equation for various capillary drain tubes and durations with 50% (weight to weight) sucrose aqueous solution at 25.91° C.
Figure 11:
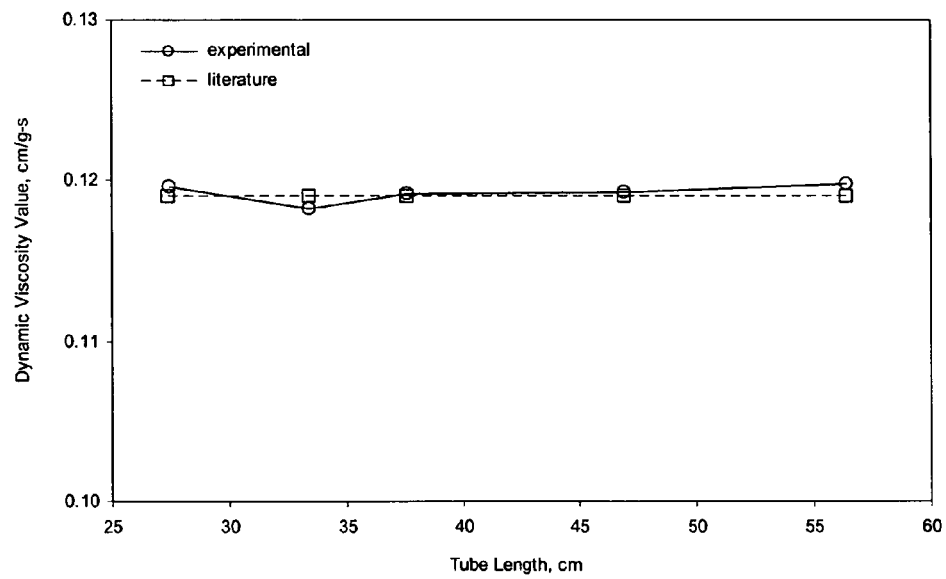
FIG. 11 shows comparison of experimentally determined dynamic viscosity values with literature viscosity values of 50% (weight to weight) sucrose aqueous solution at 25.91° C.

Using the MVC viscometer embodiment described above, viscosity values of 50% (by weight) sucrose aqueous solution as a Newtonian test fluid were determined, as shown in FIGS. 9 through 13, and three non-Newtonian fluids, a 0.2% (by weight) CMC aqueous solution, a 0.3% (by weight) CMC aqueous solution, and a 0.4% (by weight) CMC aqueous solution, were characterized, as shown in FIGS. 14 through 19. CMC (Sigma, St. Louis Mo.) aqueous solutions and the sucrose aqueous solution are chosen to test both the fabricated MVC viscometer and its viscosity equations, since both sucrose indispensable to daily life and high viscosity CMC are soluble in water, and do not inflict any health hazards (14). CMC is also used widely for various industrial products. The average molecular weight of CMC is $7\times10^6$. The viscosity values of the sucrose aqueous solution obtained with the MVC viscometer were compared against the literature values, as shown in FIG. 11. The lengths of each inner capillary drain tube 51 in the five drain tube assemblies for the MVC viscometer were 27.5 cm, 33.4 cm, 37.6 cm, 46.9 cm, and 56.4 cm; the inside diameter of each inner capillary drain tube 51 of the five drain tube assemblies was 0.1023 cm. The literature viscosity value of the sucrose aqueous solution is used to calibrate the MVC viscometer for the application of non-Newtonian fluids, since the flow behavior index of the sucrose aqueous solution is approximately one. The mass detector 33, an electronic balance with the RS232 interface and 0.001-g readability, was used to measure the collected fluid mass variation over time, m(t).

The instantaneous mass of the collected fluid was recorded in a computer data file through an analog-to-digital data acquisition system that can be represented by the processor 34. Data collection required approximately 12 minutes and 15 minutes, respectively, for sextuple viscosity measurements of 50% (by weight) sucrose aqueous solution and single characterization of the flow behavior of the CMC aqueous solutions, using the MVC viscometer. Data collection required approximately 5 minutes and 6 minutes, respectively, for 23 duplicate viscosity measurements of the sucrose aqueous solution and single characterization of the flow behavior of the CMC aqueous solutions, using the DVC viscometer.

FIGS. 9 through 19 are prepared with experimental data obtained at atmospheric pressure. Experimental data were obtained for 50% (weight to weight) sucrose aqueous solution at 25.91° C. using a MVC viscometer with drain tube lengths of 27.5, 33.4, 37.6, 46.9 and 56.4 cm. The procedures used for collecting the data were as described above. The results are shown in FIG. 9. These data were applied to the Newtonian viscosity equation as shown in FIG. 10. The slope values of the 27.5 cm capillary drain tube, the 33.4 cm capillary drain tube, the 37.6 cm capillary drain tube, the 46.9 cm capillary drain tube, and the 56.4 cm capillary drain tube are $9.6998\times10^{-6}$ s$^{-1}$, $8.0466\times10^{-6}$ s$^{-1}$, $7.0945\times10^{-6}$ s$^{-1}$, $5.6818\times10^{-6}$ s$^{-1}$, and $4.7043\times10^{-6}$ s$^{-1}$, respectively. The experimental viscosity values of the 27.5 cm inner capillary drain tube, the 33.4 cm inner capillary drain tube, the 37.6 cm inner capillary drain tube, the 46.9 cm inner capillary drain tube, and the 56.4 cm inner capillary drain tube are 0.1192 g/cm-s, 0.1183 g/cm-s, 0.1192 g/cm-s, 0.1193 g/cm-s, and 0.1198 g/cm-s, respectively. The experimental viscosity values of the sucrose aqueous solution at 25.91° C. were obtained by substituting the slope term of Equation (5) (the Newtonian viscosity equation) with the values of g=981 cm/s$^2$, $R_o$=0.05048 cm, ρ=1.2296 g/cm$^3$, R=5.5501 cm, and the respective length of the inner capillary drain tubes. The error percentages of the experimental viscosity values of the sucrose aqueous solution in comparison with the literature viscosity value of 0.1190 g/cm-s at 25.91° C. for the 27.5 cm inner capillary drain tube, the 33.4 cm inner capillary drain tube, the 37.6 cm inner capillary drain tube, the 46.9 cm inner capillary drain tube, and the 56.4 cm inner capillary drain tube are 0.14, −0.61, 0.14, 0.24, and 0.68, respectively.

Figure 12:
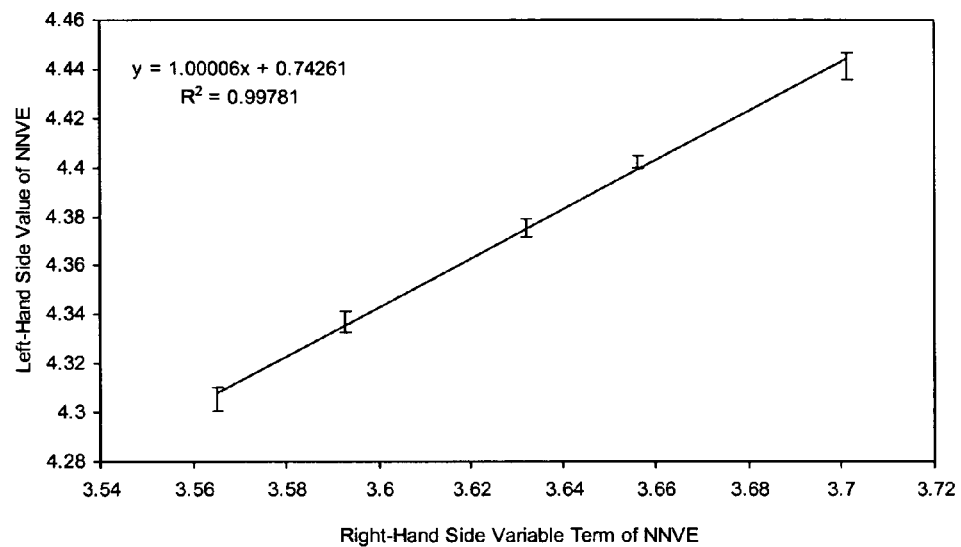
FIG. 12 shows sextuple drain amounts (in grams) of 50% (weight to weight) sucrose aqueous solution against drain durations (in seconds) applied to left-hand side (LHS) and right-hand side (RHS) variable term of non-Newtonian viscosity equation (NNVE) to determine flow behavior index n and consistency index k of the sucrose aqueous solution at 25.91° C., using one embodiment of the multiple capillary viscometer having five capillary drain tubes in different lengths.
Figure 13:
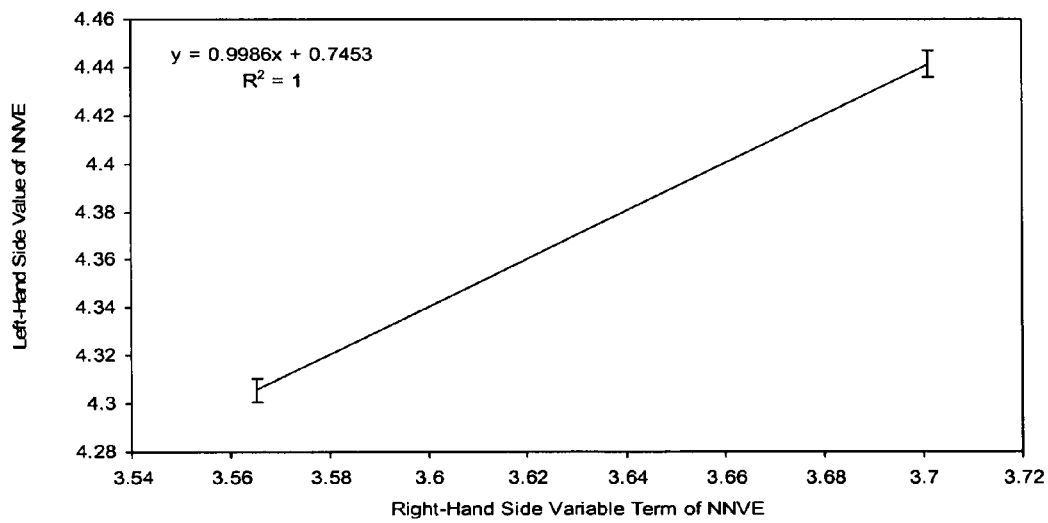
FIG. 13 shows drain amounts (in grams) of 50% (weight to weight) sucrose aqueous solution against drain durations (in seconds) applied to the left-hand side (LHS) and right-hand side (RHS) variable term of non-Newtonian viscosity equation (NNVE) to determine flow behavior index n and consistency index k of the sucrose aqueous solution at 25.91° C., using one embodiment of the dual capillary viscometer having two capillary drain tubes in different lengths.

The experimental data for 50% (weight to weight) sucrose aqueous solution shown in FIG. 9 was also applied to the non-Newtonian viscosity equation (Equation (12)), as shown in FIGS. 12 and 13. The slope value and the intercept value of the plot are 1.00006 and 0.7426, respectively, as shown in FIG. 12 with the MVC viscometer described above, whereas the slope value and the intercept value of the plot are 0.9986 and 0.7453, respectively, as shown in FIG. 13 with the DVC viscometer (having inner capillary drain tube lengths of 27.5 cm and 56.4 cm). The flow behavior index n and the flow consistency k sucrose aqueous solution at 25.91° C. are obtained by substituting the slope value and the intercept value from FIGS. 12 and 13 into Equations (13) and (14), respectively. The flow behavior index n and the flow consistency k of the sucrose aqueous solution at 25.91° C. are 0.9999 and 0.1190 g/cm-s$^{1.0001}$ from FIG. 12, using the MVC viscometer, whereas the flow behavior index n and the flow consistency k of the sucrose aqueous solution at 25.91° C. are 1.0014 and 0.1184 g/cm-s$^{0.9986}$ from FIG. 13, using the DVC viscometer.

Figure 14:
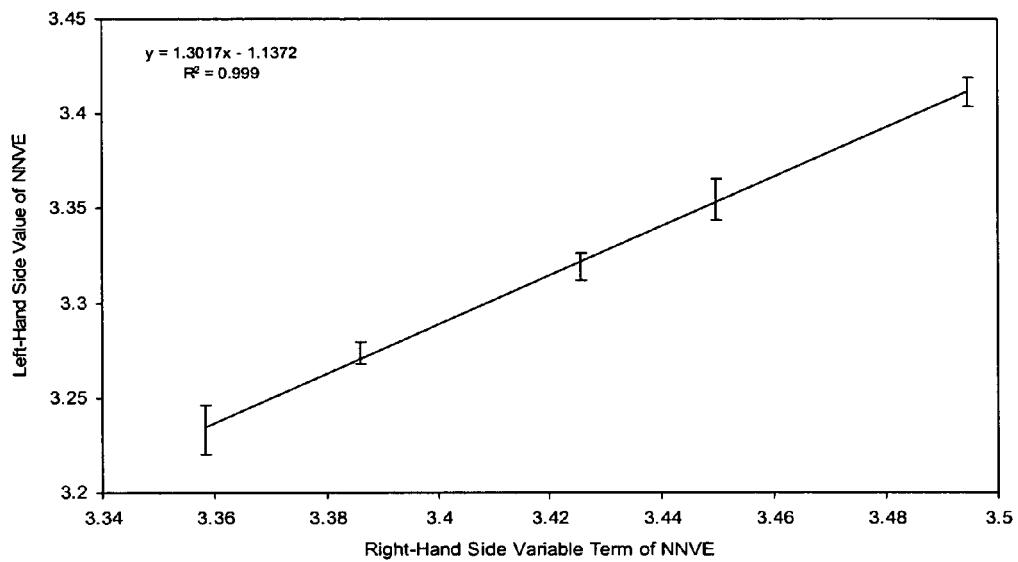
FIG. 14 shows quintuple drain amounts (in grams) of 0.2% (weight to weight) CMC aqueous solution at various drain durations (in seconds) as applied to left-hand side (LHS) and right-hand side (RHS) variable term of non-Newtonian viscosity equation for the determination of flow behavior index n and consistency index k of 0.2% CMC aqueous solution at 25.73° C., using one embodiment of the multiple capillary viscometer having five capillary drain tubes in different lengths.
Figure 15:
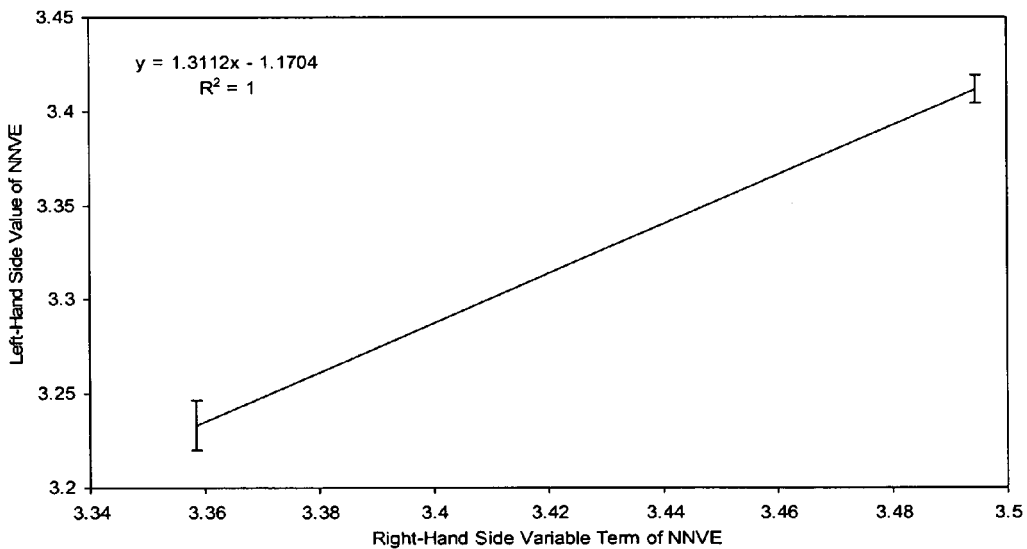
FIG. 15 shows quintuple drain amounts (in grams) of 0.2% (weight to weight) CMC aqueous solution at various drain durations (in seconds) as applied to left-hand side (LHS) and right-hand side (RHS) variable term of non-Newtonian viscosity equation (NNVE) for the determination of flow behavior index n and consistency index k of 0.2% CMC aqueous solution at 25.73° C., using one embodiment of the dual capillary viscometer having two capillary drain tubes in different lengths.

Quintuple experimental data of 0.2% (weight to weight) CMC aqueous solution were obtained using the MVC viscometer and the DVC viscometer as described above and were applied to the non-Newtonian viscosity equation, as shown in FIGS. 14 and 15. The slope value and the intercept value of the plot are 1.3017 and −1.1372 from FIG. 14, respectively, using the MVC viscometer. The slope value and the intercept value of the plot are 1.3112 and −1.1704 from FIG. 15, respectively, using the DVC viscometer. The flow behavior index n and the flow consistency k of the 0.2% CMC aqueous solution at 25.73° C. are obtained by substituting the slope value and the intercept value from FIGS. 14 and 15 into Equations (13) and (14), respectively. The flow behavior index n and the flow consistency k of 0.2% CMC aqueous solution at 25.73° C. are 0.7682 and 0.7810 g/cm-s$^{1.2318}$ using the MVC viscometer (data from FIG. 14), whereas the flow behavior index n and the flow consistency k of 0.2% CMC aqueous solution at 25.73° C. are 0.7627 and 0.8011 g/cm-s$^{1.2373}$ using the DVC viscometer (data from FIG. 15). The error percentages of the standard deviations of the left-hand side values of non-Newtonian Equation (12) at 25.73° C. for the 27.5 cm inner capillary drain tube, the 33.4 cm inner capillary drain tube, the 37.6 cm inner capillary drain tube, the 46.9 cm inner capillary drain tube, and the 56.4 cm inner capillary drain tube are 0.22, 0.33, 0.21, 0.18, and 0.41, respectively.

Figure 16:
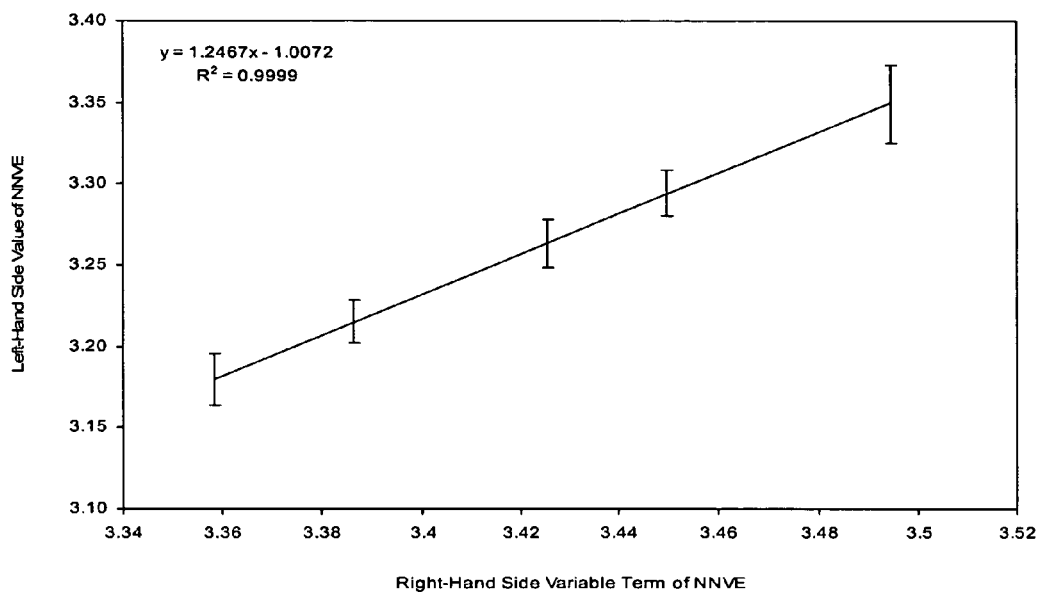
FIG. 16 shows quadruple drain amounts (in grams) of 0.3% (weight to weight) CMC aqueous solution at various drain durations (in seconds) as applied to left-hand side (LHS) and right-hand side (RHS) variable term of non-Newtonian viscosity equation (NNVE) for the determination of flow behavior index n and consistency index k of 0.3% CMC aqueous solution at 25.79° C., using one embodiment of the multiple capillary viscometer having five capillary drain tubes in different lengths.
Figure 17:
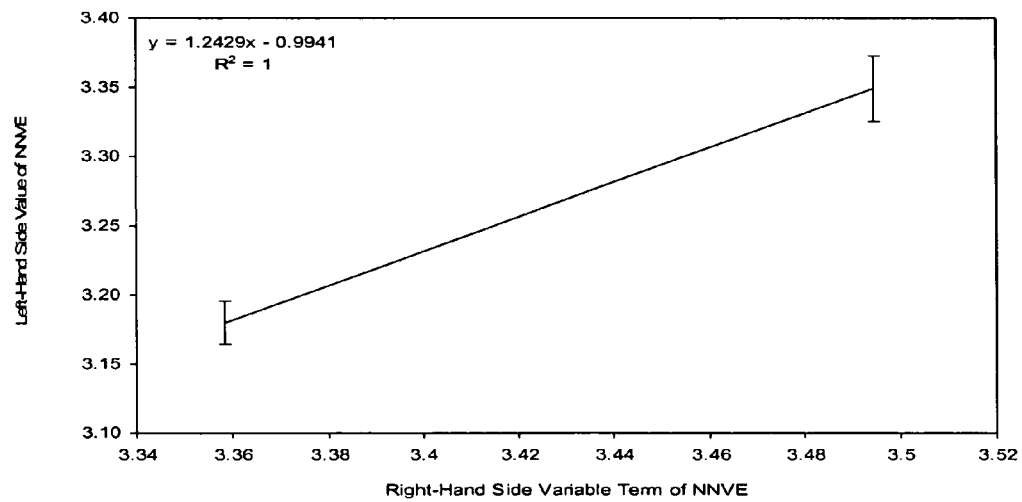
FIG. 17 shows quadruple drain amounts (in grams) of 0.3% (weight to weight) CMC aqueous solution at various drain durations (in seconds) as applied to left-hand side (LHS) and right-hand side (RHS) variable term of non-Newtonian viscosity equation (NNVE) for the determination of flow behavior index n and consistency index k of 0.3% CMC aqueous solution at 25.79° C., using one embodiment of the dual capillary viscometer having two capillary drain tubes in different lengths.

Quadruple experimental data of 0.3% (weight to weight) CMC aqueous solution were obtained using the MVC viscometer and the DVC viscometer as described above and were applied to the non-Newtonian viscosity equation, as shown in FIGS. 16 and 17. The slope value and the intercept value of the plot are 1.2467 and −1.0072 from FIG. 16, respectively, using the MVC viscometer. The slope value and the intercept value of the plot are 1.2429 and −0.9941 from FIG. 17, respectively, using the DVC viscometer. The flow behavior index n and the flow consistency k of 0.3% CMC aqueous solution at 25.79° C. are obtained by substituting the slope value and the intercept value from FIGS. 16 and 17 into Equations (13) and (14), respectively. The flow behavior index n and the flow consistency k of 0.3% CMC aqueous solution at 25.79° C. are 0.8021 and 0.7032 g/cm-s$^{1.1979}$ from FIG. 16, using the MVC viscometer, whereas the flow behavior index n and the flow consistency k of 0.3% CMC aqueous solution at 25.79° C. are 0.8046 and 0.6956 g/cm-s$^{1.1954}$ from FIG. 17, using the DVC viscometer. The error percentages of the standard deviations of the left-hand side values of non-Newtonian Equation (12) at 25.79° C. for the 27.5 cm inner capillary drain tube, the 33.4 cm inner capillary drain tube, the 37.6 cm inner capillary drain tube, the 46.9 cm inner capillary drain tube, and the 56.4 cm inner capillary drain tube are 0.71, 0.42, 0.46, 0.40, and 0.51, respectively.

Figure 18:
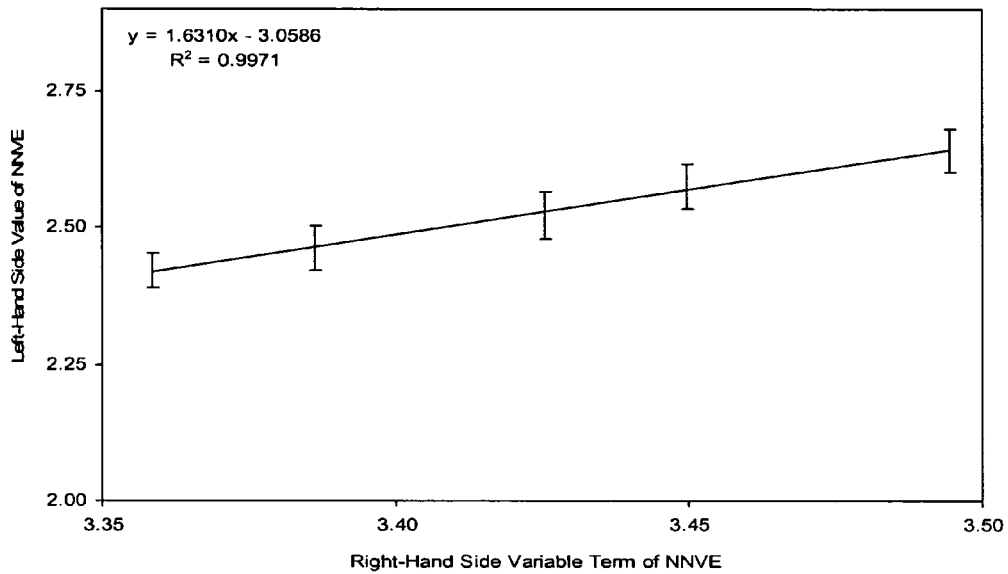
FIG. 18 shows quadruple drain amounts (in grams) of 0.4% (weight to weight) CMC aqueous solution at various drain durations (in seconds) as applied to left-hand side (LHS) and right-hand side (RHS) variable term of non-Newtonian viscosity equation (NNVE) for the determination of flow behavior index n and consistency index k of 0.4% CMC aqueous solution at 25.78° C., using one embodiment of the multiple capillary viscometer having five capillary drain tubes in different lengths.
Figure 19:
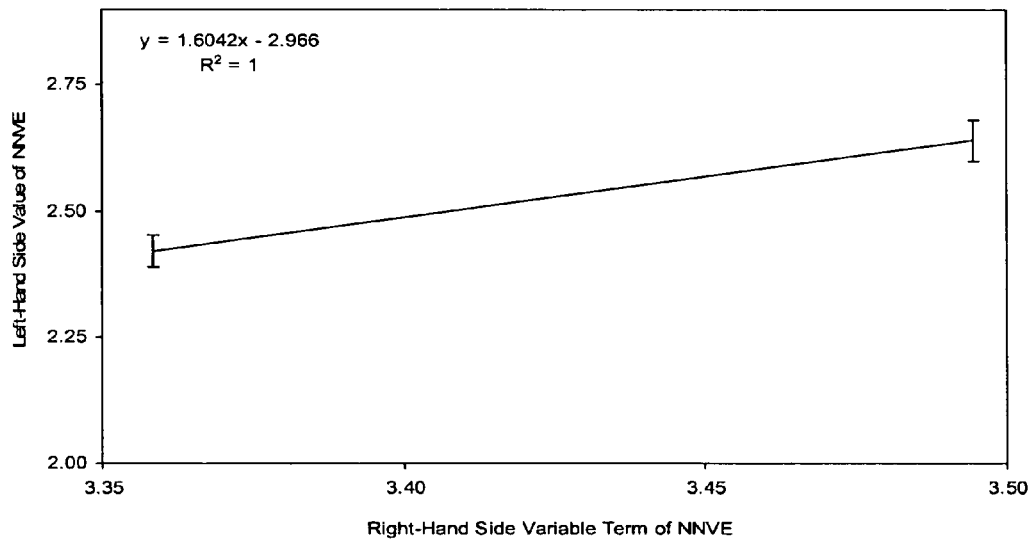
FIG. 19 shows quadruple drain amounts (in grams) of 0.4% (weight to weight) CMC aqueous solution at various drain durations (in seconds) as applied to left-hand side (LHS) and right-hand side (RHS) variable term of non-Newtonian viscosity equation for the determination of flow behavior index n and consistency index k of 0.4% CMC aqueous solution at 25.78° C., using one embodiment of the dual capillary viscometer having two capillary drain tubes in different lengths.

Quadruple experimental data of 0.4% (weight to weight) CMC aqueous solution were obtained using the MVC viscometer and the DVC viscometer as described above and were applied to the non-Newtonian viscosity equation, as shown in FIGS. 18 and 19. The slope value and the intercept value of the plot are 1.6310 and −3.0586 from FIG. 18, respectively, using the MVC viscometer. The slope value and the intercept value of the plot are 1.6042 and −2.9660 from FIG. 19, respectively, using the DVC viscometer. The flow behavior index n and the flow consistency k of 0.4% CMC aqueous solution at 25.78° C. are obtained by substituting the slope value and the intercept value from FIGS. 18 and 19 into the non-Newtonian equation as shown in Equation (12). The flow behavior index n and the flow consistency k of 0.4% CMC aqueous solution at 25.78° C. are 0.6131 and 2.4585 g/cm-s$^{1.3869}$ from FIG. 18, respectively, using the MVC viscometer, whereas the flow behavior index n and the flow consistency k of 0.4% CMC aqueous solution at 25.78° C. are 0.6234 and 2.4523 g/cm-s$^{1.3766}$ from FIG. 19, respectively, using the DVC viscometer. The error percentages of the standard deviations of the left-hand side values of the non-Newtonian viscosity Equation (12) at 25.78° C. for the 27.5 cm inner capillary drain tube, the 33.4 cm inner capillary drain tube, the 37.6 cm inner capillary drain tube, the 46.9 cm inner capillary drain tube, and the 56.4 cm inner capillary drain tube are 1.51, 1.53, 1.72, 1.63, and 1.28, respectively.

What is claimed is:

1. A capillary viscometer for the determination of a viscosity value of a Newtonian test fluid or at least one rheological parameter of a non-Newtonian test fluid, said viscometer comprising:
    a. a storage reservoir for holding said test fluid;
    b. at least one drain tube assembly, each drain tube assembly having an inner capillary drain tube, each of said inner capillary drain tubes having a first end with a first opening and a second end with a second opening, said first end opening being in fluid communication with said storage reservoir and said second end being open to the atmosphere;
    c. a collector for collecting said test fluid, said collector positioned under said second opening of each of said inner capillary drain tube;
    d. a detector in communication with said collector; and
    e. a processor in communication with said detector, said processor comprising a data acquisition software;
        wherein said detector senses a mass change caused by said test fluid accumulating in said collector and correlates said mass change against a drain duration time to create an experimental data set for each of said inner capillary drain tubes, said mass change being directly proportional to an amount of test fluid drained from each of said inner capillary drain tubes at said drain duration time;

and wherein said test fluid is a Newtonian fluid or a non-Newtonian fluid; said experimental data sets for a Newtonian are used to determine a viscosity value of said Newtonian fluid, said viscosity value being determined using a slope value, said slope value determined from a linear least squares fit of a straight line passing through an origin of a set of rectangular coordinates obtained by applying said experimental data sets to the following equation:

$$-\ln\left(1 - \frac{m}{\left(H + \frac{P_g}{\rho g} + L\right)\pi R^2 \rho}\right) = \left(\frac{gR_o^4 \rho}{8\mu R^2 L}\right)(t)$$

where g=acceleration of gravity;

H=initial level of the test fluid in said reservoir tank or height of said reservoir tank, when the reservoir tank is filled up;

L=length of the inner capillary drain tube of the drain tube assembly;

m=accumulated amount of said test fluid drained at drain duration time, t;

$P_g$=gauge pressure;

R=inside equivalent radius of said storage reservoir;

$R_o$=inside radius of said inner capillary drain tube of the drain tube assembly;

t=drain duration time;

$\rho$=density of said test fluid; and $\mu$=dynamic viscosity of said Newtonian fluid $\pi$=3.1416; and where said experimental data sets for a non-Newtonian fluid are used to determine said set of rheological parameters of said non-Newtonian fluid, said set of rheological parameters selected from the group consisting of a flow behavior index and a consistency index, said flow behavior index and said consistency index being determined using a slope value and an intercept value, respectively, said slope value and said intercept value determined from a linear least squares fit of a straight line obtained by applying said experimental data to the following non-Newtonian viscosity equation (NNVE):

$$\ln\left(\frac{m}{\pi R_o^3 \rho t}\right) \cong \frac{1}{n}\ln\left(\frac{\rho g R_o\left(H + \frac{P_g}{\rho g} + L\right)}{2L}\right) + \ln\left(\frac{n}{(1+3n)}\left(\frac{1}{k}\right)^{\frac{1}{n}}\right)$$

where k=consistency index of the power law equation;

n=flow behavior index of the power law equation; and g, H, L, m, Pg, $\pi$, Ro, t, Pg, and $\rho$ are as defined above.

2. The viscometer of claim 1 where said viscosity value is determined by applying said slope value into the following equation $$\mu = \frac{g\rho R_o^4}{8 R^2 L S}$$

where

S: slope value of Newtonian viscosity equation; and g, L, R, Ro, $\rho$, and $\mu$ are as defined in claim 1.

3. The viscometer of claim 1 where said flow behavior index is determined by applying said slope value into the following equation $$n = \frac{1}{S}$$

where

S=slope value of a linear least squares straight line generated with said non-Newtonian viscosity equation (NNVE); and n is as defined in claim 1.

4. The viscometer of claim 1 where said consistency index is determined by applying said flow behavior index value into the following equation $$k = \left(\frac{n}{\exp(I)(1+3n)}\right)^n$$

where

I=intercept value of a linear least squares straight line generated with said non-Newtonian viscosity equation (NNVE); and n and k are as defined in claim 1.

5. The viscometer of claim 1 where said experimental data sets are used to determine a shear stress value at an inner surface of said inner capillary drain tube using the following equation:

$$(\tau_{rz})\big|_{r=R_o} = \frac{\rho g R_o}{2L}\left(H + L + \frac{P_g}{\rho g} - \frac{m}{\pi R^2 \rho}\right)$$

where $(\tau_{rz})|_{r=R_o}$ = shear stress at said inner wall of said inner capillary drain tube;

r=distance from the center of a cylindrical tube; and $p_g$, $\rho$, g, H, L, m, R, and $R_o$ are as defined in claim 1.

6. The viscometer of claim 1 where said experimental data sets are used to determine a shear rate at an inner surface of said capillary drain tube using the following equation:

$$-\left(\frac{dv_z}{dr}\right)\bigg|_{r=R_o} = \left[\frac{\rho g R_o}{2kL}\left(H + L + \frac{P_g}{\rho g} - \frac{m}{\pi R^2 \rho}\right)\right]^{\frac{1}{n}}$$

where $-\left(\frac{dv_z}{dr}\right)\big|_{r=R_o}$ = shear rate of said test fluid at said inner wall of said inner capillary drain tube;

g, H, L, m, R, $R_o$, $P_g$, $\pi$ and $\rho$ are as defined in claim 1;

n and k are as defined in claim 1;

r=the distance from the center of a cylindrical tube; and $v_z$ is local velocity of said test fluid in said inner capillary drain tube at a distant r from the center of the tube.

* * * * *